United States Patent [19]

Chu

[11] 4,347,355
[45] Aug. 31, 1982

[54] INHIBITORS OF TRANSPEPTIDASE

[75] Inventor: Daniel T. Chu, Vernon Hills, Ill.

[73] Assignee: Abbott Laboratories, North Chicago, Ill.

[21] Appl. No.: 212,006

[22] Filed: Dec. 1, 1980

Related U.S. Application Data

[63] Continuation-in-part of Ser. No. 123,142, Feb. 21, 1980, abandoned.

[51] Int. Cl.$^3$ ............................................. C07D 487/04
[52] U.S. Cl. .............................. 542/420; 260/245.2 T; 260/326.46; 544/373; 546/123; 546/272
[58] Field of Search ................. 260/245.2 T; 542/420; 546/272, 123; 544/373

[56] References Cited

U.S. PATENT DOCUMENTS

| | | | |
|---|---|---|---|
| 4,013,648 | 3/1977 | Horning et al. | 260/245.2 T |
| 4,218,459 | 8/1980 | Cama et al. | 260/245.2 T |
| 4,218,463 | 8/1980 | Christensen et al. | 260/245.2 T |
| 4,251,524 | 2/1981 | Feyen et al. | 424/274 |
| 4,262,009 | 4/1981 | Christensen et al. | 260/245.2 T |
| 4,298,741 | 11/1981 | Christensen et al. | 260/245.2 T |
| 4,312,871 | 1/1982 | Christensen et al. | 260/245.2 T |

Primary Examiner—Mary C. Lee
Attorney, Agent, or Firm—Paul D. Burgauer; Dennis K. Shelton

[57] ABSTRACT

New β-lactams of the general structure:

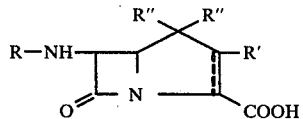

wherein R represents H or an acyl moiety known from the penicillin or cephalosporin art, R' is hydrogen, loweralkoxy, loweralkoxyalkyl, loweralkyl, phenylthio or loweralkylmercapto R" is loweralkyl, the broken line represents an optional double bond, and acyloxymethyl esters thereof. All compounds are effective antibacterials.

3 Claims, No Drawings

INHIBITORS OF TRANSPEPTIDASE

BACKGROUND OF THE INVENTION

This application is a continuation-in-part of U.S. Ser. No. 123,142, filed Feb. 21, 1980 now abandoned.

DETAILED DESCRIPTION OF THE INVENTION

Many cephalosporin and penicillin derivatives have been synthesized in the past 30 years and many of them have found their way into the arsenal of anti-biotic drugs with a broad spectrum of antibacterial activity. However, the bacteria combatted in this fashion have learned to adapt to the attacks by these antibiotics and have formed strains resistant to the antibiotics. It is therefore of great importance to find new antibiotics to which resistance has not yet developed in infectious bacteria. Basic changes in the structure of known antibiotics are particularly well suited to overcome the bacterial resistance to known therapeutics.

The present invention is thus concerned with new antibacterials, compounds of the formula:

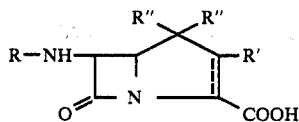

wherein R represents H or an acyl moiety known from the penicillin or cephalosporin art, R' is hydrogen, loweralkoxy, loweralkoxyalkyl, loweralkyl, phenylmercapto or loweralkylmercapto, R" is loweralkyl, the broken line represents an optional double bond, and acyloxymethyl esters thereof. Acyl groups found particularly useful are phenacetyl, phenoxyacetyl, cyanoacetyl, thenylacetyl, p-hydroxyphenylmalonoyl, α-aminophenacetyl, α-sulfophenacetyl, N-benzoylglycyl-phenylglycyl, a moiety of the formula

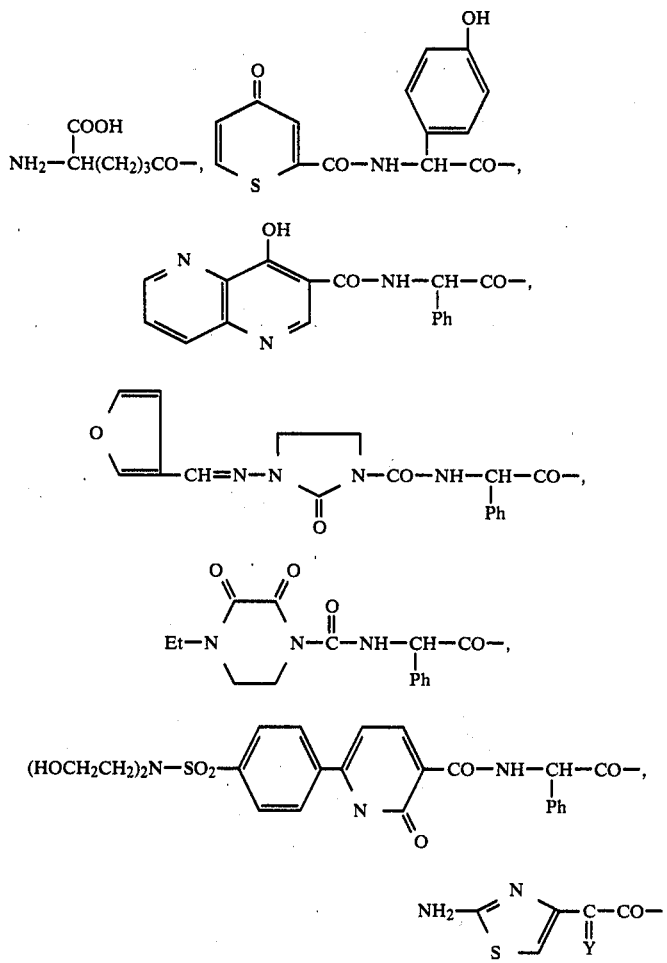

wherein Y is O or NOR", or a mercaptoacetyl of the formula R°SCH₂CO- wherein R° is phenyl, 4-pyridyl, 2-chloro-2-butenyl, allyl or n-butyl.

The compounds wherein R≠H and R' is phenylmercapto or alkoxy and the 2,3-positions are connected by a single bond are less active than the corresponding unsaturated compounds. All the compounds, however, show activity against numerous infectious and other bacteria, as can easily be demonstrated on cultures of pseudomonas strains at concentrations of 1 to 500 ppm. The new compounds will completely prevent any further growth of *Staph. aureus* and in the higher concentration ranges mentioned will produce a bacteriocidal effect.

The above compounds are prepared by the following scheme:

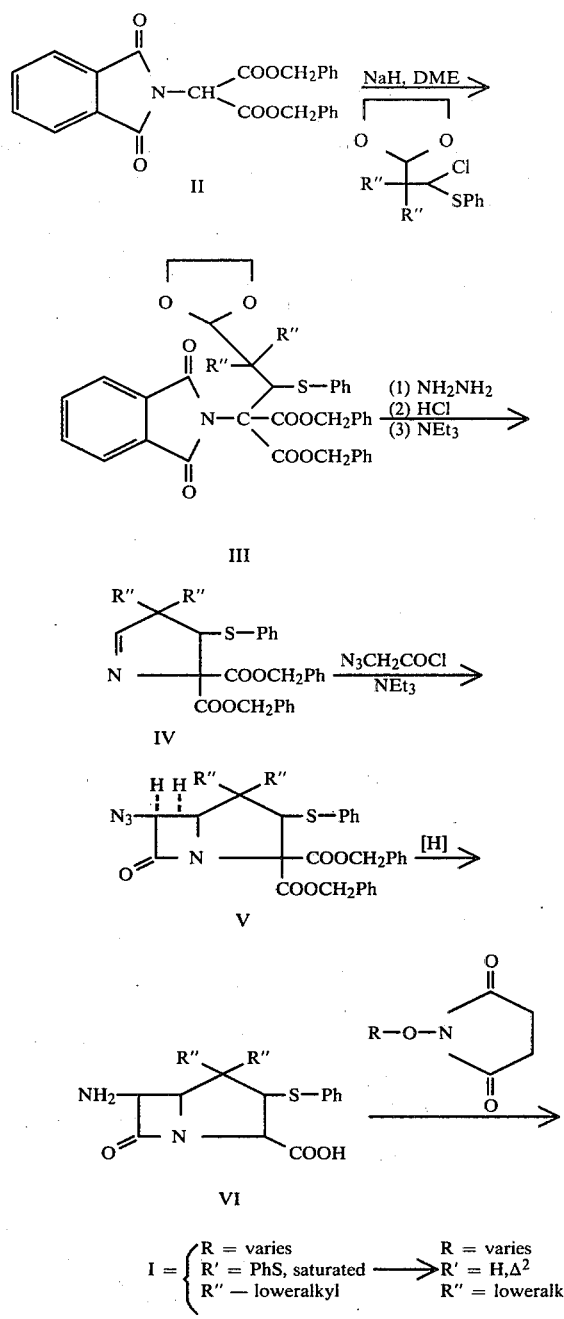

In order to illustrate the manufacture of the compounds of this invention, reference is made to the following examples which, however, are not to be interpreted as limitations of the scope of this invention. In all instances, microanalyses are used to verify the indentity of the expected compounds.

EXAMPLE 1

(a) To a cold solution of 13.1 g of dibenzyl phthalimidomalonate in 300 ml dry dimethoxyethane (DME) is slowly added 1.47 g of a 50% sodium hydride-in-oil suspension. After stirring at room temperature for 30 min., 16.2 g 1-chloro-1-phenylthio-2,2-dimethyl-3-ethylenedioxypropane is added and the mixture is refluxed 30 hrs. and then filtered. The filtrate is condensed under reduced pressure to a volume of 50 ml. This concentrate is added to 250 ml of ice-cold water and extracted with three 200 ml portions of $CH_2Cl_2$. The organic phase is dried over $MgSO_4$, evaporated, and the obtained oil is chromatographed over florisil to produce III (R''=$CH_3$) in good yield.

(b) A solution of 6.6 g of the dibenzylester acetal III in 30 ml THF is refluxed with 500 mg hydrazine hydrate for 90 min. The resulting mixture is poured into ice-cold water and extracted with $CH_2Cl_2$. The original phase is purified over an alumina column to give the substituted malonic ester III wherein the phthalimino group is replaced by the amino group and R'' is methyl. A solution of 5.3 g of this aminoester in 30 ml THF is then refluxed for 2 hrs. with 30 ml aqueous 0.5 N HCl. After evaporating the mixture under reduced pressure and placing the residue in 60 ml $CH_2Cl_2$; 1.5 ml of triethylamine and 50 g anhydrous $MgSO_4$ are added and the mixture is allowed to stand overnight. Upon subsequent filtration, washing with cold water and evaporation, 4.5 g of the cyclic diester IV is obtained as an oil in excellent yield.

(c) A solution of 9.5 g IV in 200 ml dry $CH_2Cl_2$ is cooled to $-10°$ C. in an ice-methanol bath before 2.8 ml of triethylamine is added, followed by a dropwise addition of a solution of 2.4 g azidoacetyl chloride in 35 ml $CH_2Cl_2$ over a period of 15 min. The mixture is then stirred another 15 min. and washed with water. Workup in the fasion of (a) above produces a moderately high yield of V (R''=Me).

(d) To a solution of 5.6 g of the azidoester V in 100 ml glacial acetic acid, 500 mg 10% Pd-on-carbon is added and the mixture is hydrogenated at room temperature for 1 hr., at which time the mixture is filtered and the filtrate is heated for 3 hrs. at 60° C. Solvent removal produces a moderately high yield of 6-amino-1,1-dimethyl-2-phenylthio-4-azabicyclo[2,0,3]heptane-5-one-3-carboxylic acid (VI;R''=Me).

EXAMPLE 2

(a) To an ice-cold solution of 3 g of compound VI of Example 1 and 1.68 $NaHCO_3$ in 50 ml of water is added 2.5 g o N-(phenoxymethylcarbonyloxy)-succinimide in 50 ml dimethoxyethane. The mixture is stirred for 3 hrs. and the volume is then reduced to about 10 ml under reduced pressure. Water is added and the mixture is extracted with $CH_2Cl_2$. The aqueous phase is acidified with HCl to pH 6 which produces 1.1-dimethyl-6-phenoxy-acetylamino-2-phenylthio-4-azabicyclo[2,0,3-]heptan-5-one-3-carboxylic acid in excellent yield.

(b) A solution of 4.4 g of this material in 100 ml $CH_2Cl_2$ is stirred with 1.7 m-chloroperbenzoic acid for 16 hrs., before adding 2.2 g of chlorotrimethylsilane and 3 g of triethylamine and refluxing this mixture for 5 hrs. The reaction product is diluted with water and extracted with ether. The organic phase is dried over $MgSO_4$ and evaporated to produce a solid residue. Repeated precipitation of this crude material from ether/pentane produces pure 1,1-dimethyl-6-phenoxyacetylamino-4-azabicyclo[2,0,3]2-hepten-5-one-3-carboxylic acid in a moderate yield.

EXAMPLE 3

By following the preceding Example but substituting the above succinimide with 4.1 g of 1-phenyl-1-(4-ethyl-2 3-dioxo-1-piperazinyl) carboxamidoacetoxy succinimide, one obtains I where R is

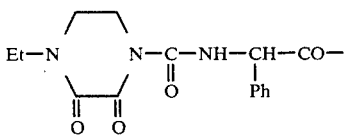

R' is phenylthio, R" is methyl and the 5-membered ring is saturated. Further following Example 2 produces moderate yields of I wherein R and R" have the above meaning, R' is H and the 2-3 positions are connected by a double bond.

EXAMPLE 4

In the described fashion of Example 2, using 5.9 g of

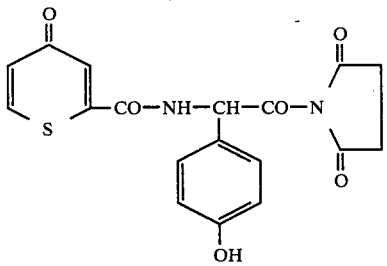

in place of the mentioned succinimide, the correspondingly N-substituted derivatives I are obtained: in the first step, R' is Ph—S— and the ring is saturated; in the second step, R' becomes H while introducing ring unsaturation (R and R" being as described) with R" being methyl in both instances.

EXAMPLE 5

1.36 of sulfophenylacetyl chloride in 10 ml ether is dropwise added to a stirred solution of 1.5 g of VI from Example 1 in 50 ml of water containing 200 mg NaOH and 850 mg NaHCO$_3$ at 0°-5° C. After 30 min., the organic layer is removed and the pH of the aqueous phase is adjusted to 6, followed by lyophylization of the acidified solution. Crystallization from water-pyridine-acetone produces the N-sulfophenylacetyl derivatives of VI (R° and R" as before, no double bond) as colorless needles. Proceeding in the fashion shown in Example 2, compound I is obtained (R=NaO$_3$S-CHPh—CO—, R'=H, R"=Me with double bond 2-3) in moderate yield.

EXAMPLE 6

An ice-cold solution of 2.8 g of the compound of Example 1(d) is mixed with 1.68 g NaHCO$_3$ in 50 ml of water. This mixture is stirred for 3 hrs. with 4 g of the succinimide ester of benzoylglycyl-phenylglycine in 50 ml of dimethoxyethane. The solvent is stripped to about 10 ml under reduced pressure and water is added followed by extraction with CH$_2$Cl$_2$. The aqueous phase is acidified with HCl to pH 3, forming a precipitate identified as 6-(N-benzoylglycylphenylglycylamino)-1,1-dimethyl-2-phenylthio-4-azabicyclo[2,0,3]heptan-5-one-3-carboxylic acid. By treating this material as in Example 2(b), the compound of structure I is obtained wherein R is N-benzoylglycylphenylglycyl, R'=H, R"=Me and the 5-membered ring is unsaturated in good yield.

EXAMPLE 7

By replacing the succinimide used in Example 6 with the succinimide of the acid of structure

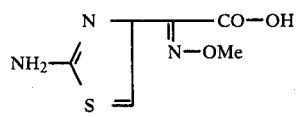

wherein the amino group is protected by the triphenylmethyl group, one obtains initially the compound of I (R is the acyl group of VII, R' is phenylmercapto and R" is Me) and after treatment with m-chlorobenzoic acid, the 2-substituent is removed while a double bond is introduced simultaneously into the 5-membered ring.

EXAMPLE 8

(a) To 4.4 g of the product of Example 2(a) in 40 ml of DMF is added 480 mg sodium hydride as a 50% oil suspension and after 15 min. of stirring, 1.7 g benzylbromide together with a catalytic amount of tetrabutylammonium iodide are added. The mixture is stirred for 4 hrs. and poured into water. Extraction of the aqueous mixture with CH$_2$Cl$_2$, drying the extract with MgSO$_4$ and evaporation produces an oil which is purified on neutral almina; it is identified as the benzyl ester of the compound of Example 2(a).

(b) Treating 5.3 g of this compound in 20 ml carbon tetrachloride with 1.33 g of N-chlorosuccinimide under a sun lamp and with stirring for 5 hrs., filtering the mixture and evaporation produces the 2-chloro-2-phenylmercapto analog of the described benzyl ester in excellent yield calculated from the compound of Example 2(a).

(c) A solution of 5.6 g of this compound in 50 ml CH$_2$Cl$_2$ is heated for 3 hrs. with 1.1 g of triethylamine. The mixture is then washed with cold water. The organic layer is dried and evaporated to produce a nearly theoretical amount of the analog of the compound of (a) above but containing a double bond between the 2-3 positions.

(d) A solution of 1.33 g anhydrous AlCl$_3$ in nitromethane is added to a solution of 5.3 g of the compound of (c) above in 2 g anisole and 20 ml CH$_2$Cl$_2$ under ice cooling. After stirring at room temperature for 5 hrs., the mixture is diluted with ethyl acetate, washed with dilute HCl and extracted with 5% aqueous NaHCO$_3$. The aqueous extract is acidified with HCl and then extracted with ethyl acetate. The original layer is washed with water, dried over MgSO$_4$ and evaporated to give a solid residue. After recrystallization from acetone/pentane, the pure unsaturated compound I (R=phenoxyacetyl, R'=phenylmercapto, R"=Me) is obtained in good yield.

EXAMPLE 9

(a) When 5.3 g. of the compound of example 8(c) in 50 ml of methanol is stirred with 2.1 g soldium metaperiodate at 0° C. for 5 hrs. followed by refluxing for 15 hrs., evaporation and the CH$_2$Cl$_2$ extraction procedure of Example 1(a), the analog of Example 8(c) is obtained in good yield, carrying a methoxy group in the 2-position in place of the phenylmercapto group.

(b) Removal of the ester group is carried out as in Example 8(d) to produce a good yield of the 2-3 unsaturated I (R=phenoxyacetyl, R'=methoxy, R"=Me).

EXAMPLE 10

To a solution of 4.5 g. of the compound of Example 9(a) in 30 ml CH₂Cl₂ is added a mixutre of 0.75 ml ethanethiol and 1 ml triethylamine. Refluxing for 15 hrs. and evaporation under reduced pressure produces the ethylmercapto-Δ²-analog of the compound of Example 8(c) in almost quantitative yield.

Upon ester group removal as in Example 8(d), unsaturated compound I (R=phenoxyacetyl, R'=EtS, R"=Me) is obtained in very good yield.

EXAMPLE 11

By following the procedure of Example 9(a) and 9(b) with 5.6 g of the compound of Example 8(c) but using 20 ml of methoxyethanol in place of methanol, compound I (Δ², R=phenoxyacetyl, R'=MeOCH₂CH₂O, R"=Me) is obtained in good yield.

EXAMPLE 12

To a solution of 5.6 g of the compound of Example 8(b) in 100 ml dry THF at 0° C. is added 3.33 ml of a 3-molar solution of methylmagnesium chloride. After stirring for 1 hr., 2.1 g sodium periodate is added and the mixture is refluxed for 15 hrs. This is followed by the usual workup using CH₂Cl₂ and a carbon column to produce an oil identified as I wherein R is phenoxyacetyl, R' and R" are methyl, the 5-membered ring is unsaturated and the carboxy group is esterified with benzyl.

Removal of the benzyl ester group in the fashion of Example 8(d) produces the unsaturated compound I (R=phenoxyacetyl, R'=R"=Me).

EXAMPLE 13

To 3.2 g of the product in Example 2(b) in 25 ml DME is added 480 mg sodium hydride as a 50% oil suspension and, after 5 minutes of stirring, 1.5 g chloromethyl pivalate is added. After 2½ hrs. the mixture is evaporated and the residue is redissolved in methylene chloride, washed with water, dried and evaporated. It is purified through column chromatography on aluminum, yielding the pivaloxymethyl ester of 2(b) (R=PhOCH₂CO; R'=H; R"=CH₃).

EXAMPLE 14

In the described procedure as in Example 13, using α-pivaloxy ethyl chloride instead of chloromethyl pivalate, the α-pivaloxy ethyl ester of 2(b) (R=PHOCH₂CO, R'=H, R"=CH₃) is obtained.

By following Example 13 but substituting the product of Example 2(b) by the compounds of Examples 3-12, the corresponding pivaloxymethyl esters of the shown free acids are obtained.

In similar fashion, the use of the succinimino esters or acid chlorides of various other acyl groups frequently used in the cephalosporin or penicillin series, leads to the saturated compounds of structure I wherein R' is phenylthio, alkyoxy, alkylthio, alkoxyalkyl and R" is any loweralkyl, and ultimately to the 2-3 unsaturated (or Δ²) compounds and their acyloxymethyl esters with R'=H, alkyl, phenylmercapto, alkoxy, alkylmercapto or alkoxyalkoxy, showing the following acyl groups in the 6-position:

R = phenacetyl
= phenoxyacetyl
= cyanoacetyl
= thenylacetyl
= p-hydroxyphenylmalonoyl
= α-aminophenacetyl
= α-sulfophenylacetyl
= aminothiazylacetyl
= 5 aminoglutaroyl

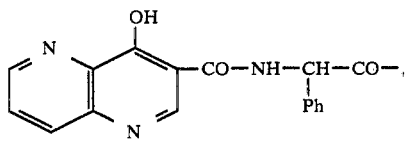

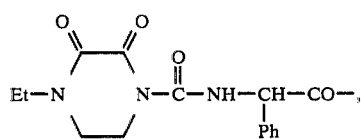

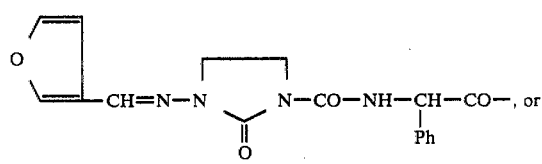

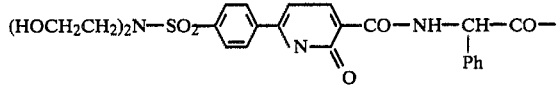

In all cases, the saturated and unsaturated 2-substituted or unsubstituted compounds, are active against pseudomonas. The 2-unsubstituted compounds are best obtained from the 2-phenylmercapto-Δ²-compounds in yields of 65-80% and ordinarily are more active, i.e., they require a lower dosage than the 2-phenylmercapto compounds. In vitro activity of the latter compounds are generally found at 100-500 ppm; the unsaturated analogs are active at 1-250 ppm against numerous infectuous, gram-positive bacteria.

One of the most important steps of the reaction sequence leading to the new compounds of this invention is the ring closure step for the azetidine ring. The preferred method for this reaction consists in treating compound IV in an inert organic solvent, for instance methylene chloride or DME, with an azidoacetyl halide in the presence of an acid acceptor at a temperature below room temperature, preferably between −25° C. and +10° C. Azidoacetyl chloride is an excellent agent for this reaction, although corresponding other acylating agents derived from azidoacetic acid are equally useful. Acid acceptors include trialkylamines, such as trimethylamine or triethylamine. The obtained azidoester V is then easily converted to the desired bicyclic, primary amine VI, by hydrogenating V. A preferred method for this step is catalytic hydrogenation, using a noble metal catalyst, although Raney nickel can also be used. Among noble metals, palladium is preferred, although platinum or ruthenium can be used as well.

We claim:

1. A compound of the formula

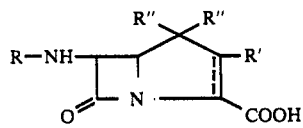

wherein R is hydrogen or acyl selected from the group consisting of phenacetyl, phenoxyacetyl, cyanoacetyl, thenylacetyl, p-hydroxyphenylmalonoyl, α-sulfophenacetyl, N-benzoylglycylphenylglycyl, a moiety of the formula

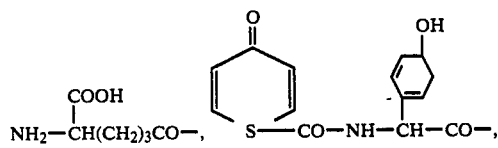

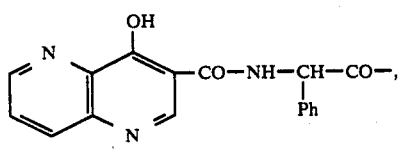

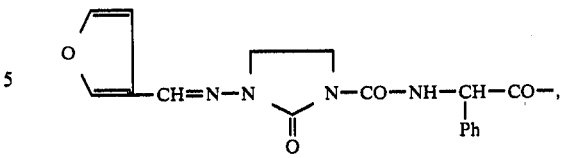

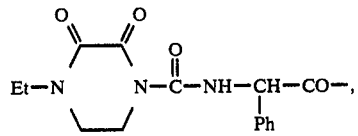

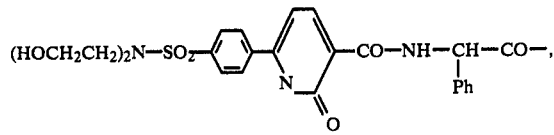

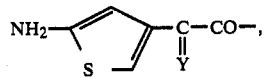

wherein Y is O or NOR″, and a mercaptoacetyl of the formula R°SCH₂CO— wherein R° is phenyl, 4-pyridyl, 2-chloro-2-butenyl, allyl or n-butyl, R′ is hydrogen, loweralkyl, loweralkoxyalkyl, loweralkoxy, loweralkylmercapto or phenylmercapto, each R″ is loweralkyl, and the broken line represents an optional double bond, and pivaloxymethyl esters thereof.

2. An unsaturated compound of claim 1 wherein R is H.

3. A compound of claim 2 wherein each R″ is methyl.

* * * * *